United States Patent [19]

Koizumi

[11] Patent Number: 4,998,065
[45] Date of Patent: Mar. 5, 1991

[54] NON-DESTRUCTIVE SECTIONAL SHAPE INSPECTING METHOD AND APPARATUS

[75] Inventor: Hideaki Koizumi, Katsuta, Japan
[73] Assignee: Hitachi, Ltd., Tokyo, Japan
[21] Appl. No.: 369,253
[22] Filed: Jun. 20, 1989

[30] Foreign Application Priority Data

Jun. 23, 1988 [JP] Japan .................................. 63-155197

[51] Int. Cl.⁵ ............................................. G01R 33/20
[52] U.S. Cl. ....................................... 324/309; 324/318
[58] Field of Search ............... 324/300, 301, 302, 303, 324/307, 309, 318, 321, 322; 128/653

[56] References Cited

U.S. PATENT DOCUMENTS

| | | | |
|---|---|---|---|
| 4,528,510 | 7/1985 | Loeffler et al. | 324/309 |
| 4,551,678 | 11/1985 | Morgan et al. | 324/300 |
| 4,581,582 | 4/1986 | Redington | 324/309 |
| 4,613,819 | 9/1986 | Chui | 324/318 |
| 4,625,168 | 11/1986 | Meyer et al. | 324/318 |

Primary Examiner—Michael J. Tokar
Attorney, Agent, or Firm—Antonelli, Terry, Stout & Kraus

[57] ABSTRACT

A non-destructive sectional shape inspecting apparatus and method. An object to be inspected is internally and/or externally filled with a material capable of reradiating a nuclear magnetic resonance signal, whereon high frequency pulses and gradient magnetic fields are applied to obtain a nuclear magnetic resonance signal which is processed into an image signal. A portion of the image signals where no nuclear magnetic resonance signal makes appearance is extracted to be utilized for plotting the sectional shape of the object under test.

28 Claims, 4 Drawing Sheets

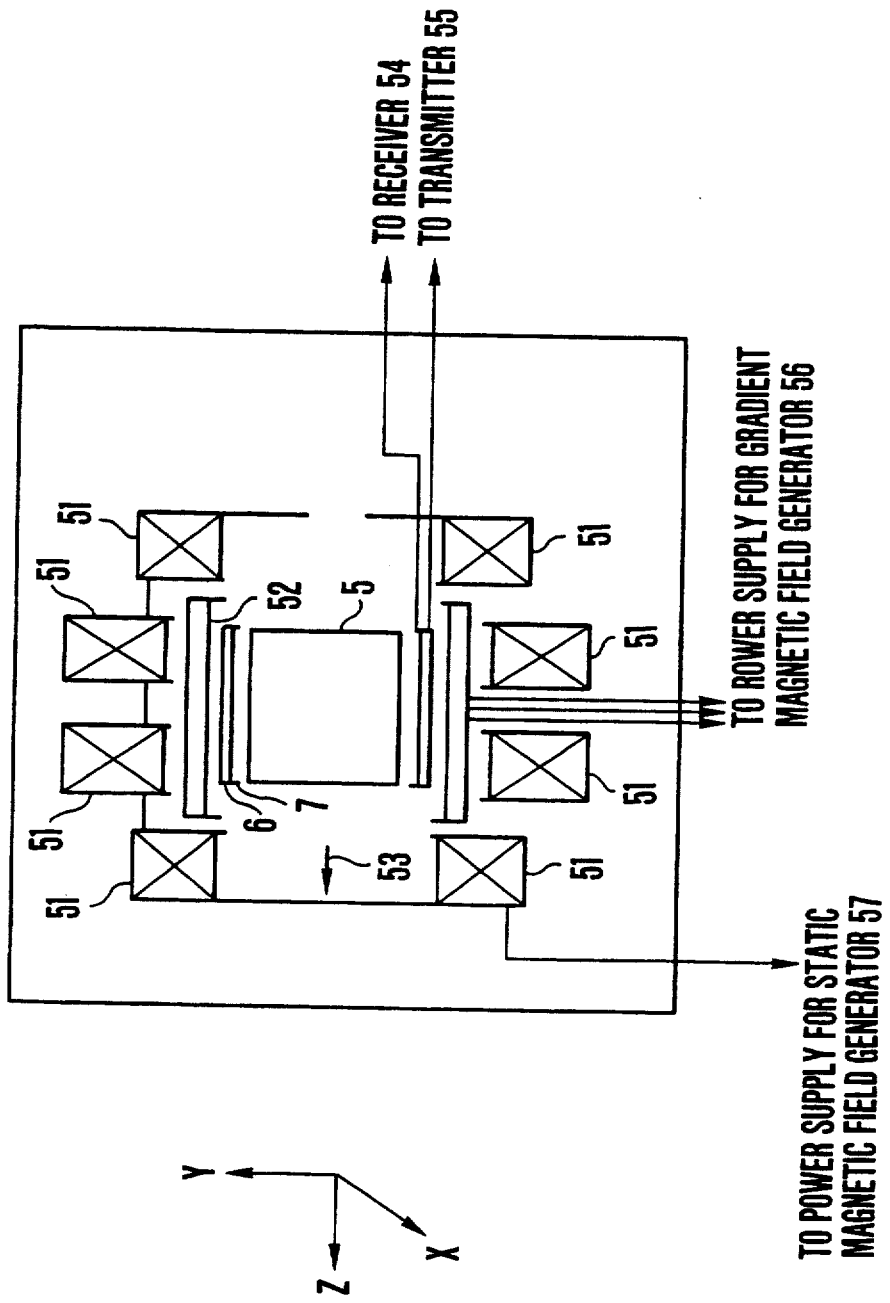

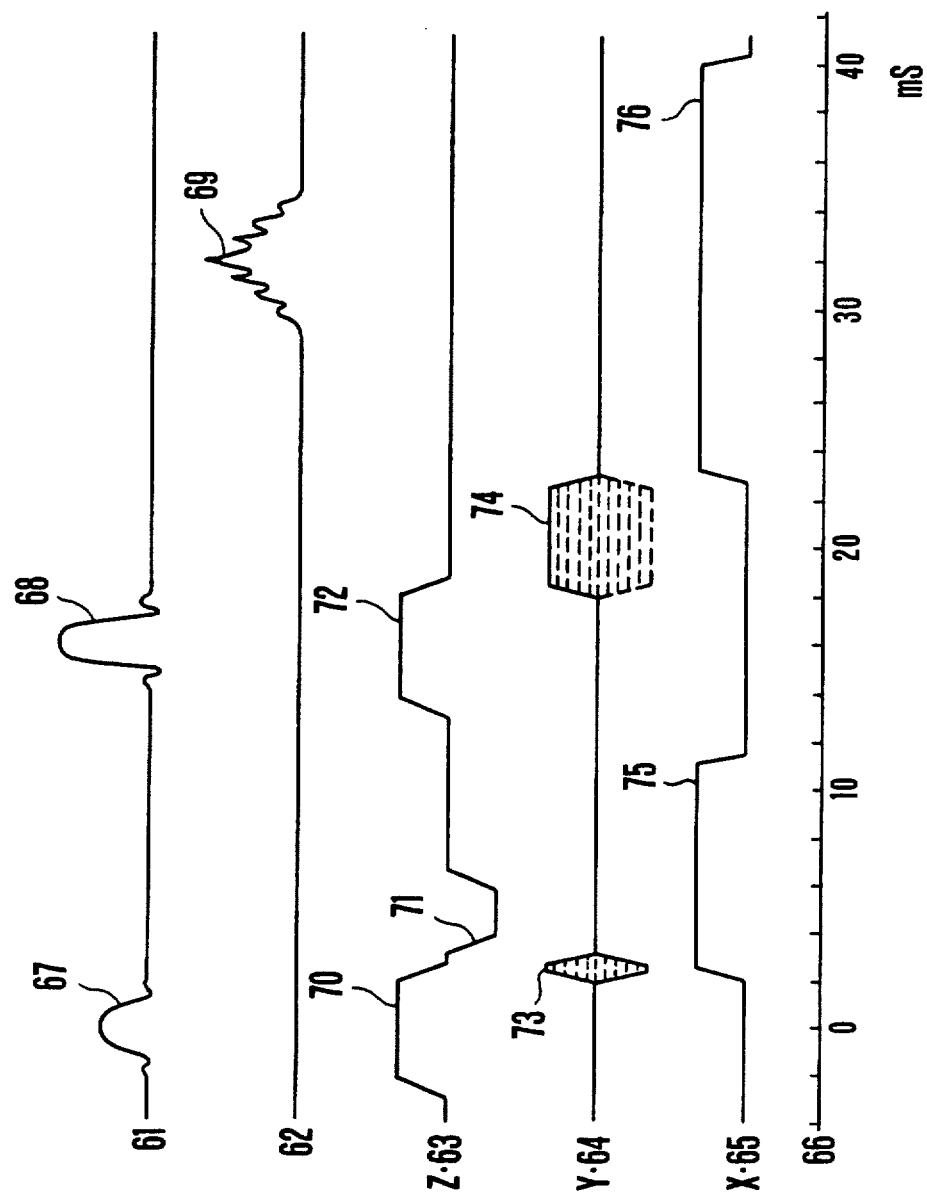

NON-DESTRUCTIVE SECTIONAL SHAPE INSPECTING METHOD AND APPARATUS

BACKGROUND OF THE INVENTION

The present invention relates to a method and apparatus for inspecting and/or determining sectional shapes, sizes and others of products formed of synthetic resins, ceramics or the like.

Heretofore, as an image diagonosis system for inspecting and determining plane sections of an object or body, there has been determining plane sections of an object or body, there has been employed a CT (computer tomography) system in which X-ray radiation is made use of. According to this system, laminographic images to be displayed are reconstituted on the basis of X-ray absorption data. When an image of the interior of an object such as, for example, a cerebrum enclosed by the skull exhibiting a high X-ray absorptance is to be reconstituted, the signals indicating X-ray absorptances at various locations of the internal or cerebrum become very feeble, because about 90% of the X-ray radiation is absorbed by the skull. When these feeble signals are enhanced, there makes appearance an artifact image similar to a ghost signal of a television system under the influence of the signals having high intensity generated at the skull, giving rise to a problem that difficulty is encountered in an attempt for extracting the image of plane sections of the cerebrum with a satisfactory definition. The problem of appearance of the artifact image is common to all objects or products each made of materials having significant difference in respect to the X-ray absorptance. Naturally, difficulty is also encountered in taking an image of the interior of a product formed of a synthetic resin incapable of absorbing the X-rays.

SUMMARY OF THE INVENTION

An object of the present invention is to solve the problems of the prior art techniques mentioned above and provide a method and an apparatus which are capable of inspecting as to injuries, damages, deformations, thickness and others the plane sections of an object formed of a synthetic resin substantially incapable of absorbing the X-rays or of an object enclosed by a ceramic material exhibiting a high X-ray absorptance.

In view of the above object, it is proposed according to an aspect of the present invention that in object to be inspected is internally and/or externally filled with a material capable of emitting a nuclear magnetic resonance (NMR) signal, which is then detected to be processed into an image signal, wherein portions of the image signal in which no NMR signal makes appearance are utilized for plotting a sectional shape of the object under test. To this end, there is provided according to a general feature of the invention a non-destructive section inspecting apparatus which comprises a cell in which an object to be inspected is disposed and which cell is filled with a material capable of emitting or reradiating a nuclear magnetic resonance signal so as to enclose the object, a high frequency radiation unit for irradiating the cell with a high frequency which is a species of electromagnetic wave for thereby generating a nuclear magnetic resonance signal, a signal detector for receiving the nuclear magnetic resonance signal, and an image processor for processing the signal into an image signal, wherein a sectional shape of the object is extracted from the image signal to be displayed.

In case where the object itself can emit a nuclear magnetic resonance signal which is however of too low level to obtain a satisfactory planigraph, the object is internally and/or externally filled with a material capable of emitting a nuclear magnetic resonance signal having higher intensity than that of the object, wherein the nuclear magnetic resonance signal of that material is detected.

With the arrangement described above, signals generated due to the nuclear magnetic resonance phenomenon at individual spatial points can be available in contrast to the X-ray tomography in which the X-ray absorption phenomenon is made use of. Thus, by processing the signal into an image signal and extracting those portions of the image signal where the nuclear magnetic resonance signal is absent or feeble, it is possible to plot the sectional shape of the object under test.

According to the invention, even the interior of an object which is enclosed by a nuclear magnetic resonance or NMR signal source can be imaged without being accompanied with generation of the artifact image. Even the interior of a bag-like object (i.e. an object having a hollow interior) can be imaged with an improved accuracy by filling internally and externally the object with a material capable of emitting the NMR signal.

It is possible according to the present invention to image the shapes of plane sections of an object made of a material incapable of emitting the NMR signal. The principle of the invention can be applied to the tomographical inspection of objects made of any materials except for an electrically high conductive material which exerts influence to the nuclear magnetic resonance phenomenon. In other words, a bag-like object exhibiting a high X-ray absorptance which has heretofore been difficult to inspect as well as a bag-like object capable of emitting only a feeble NMR signal can be inspected in respect to the shapes, dimensions or sizes of the plane sections in a non-destructive manner.

BRIEF DESCRIPTION OF THE DRAWINGS

FIG. 3 is a sectional view showing a structure of a NMR signal generating and sensing part of the apparatus shown in FIG. 2; and FIG. 4 is a timing chart showing, by way of example, a sequence of pulse signals.

DESCRIPTION OF THE PREFERRED EMBODIMENTS

In the following, the present invention will be described in detail in conjunction with an exemplary or preferred embodiment thereof by reference to the accompanying drawings.

Figure 1A:
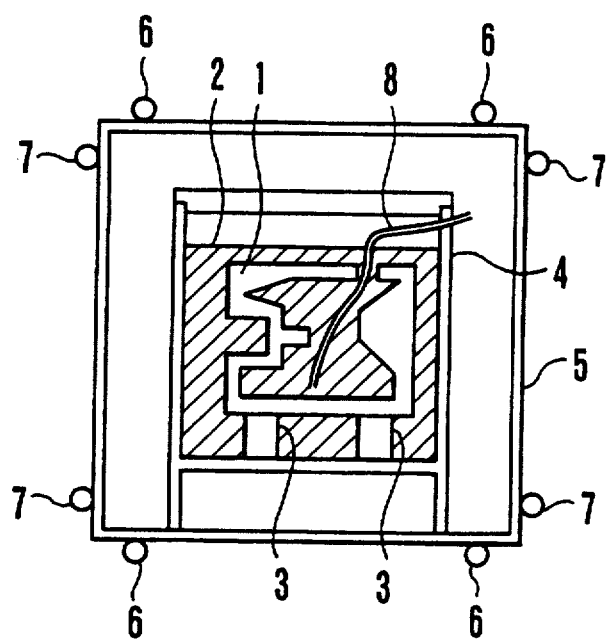
FIG. 1A is a sectional view showing a major part of the non-destructive inspecting apparatus according to an exemplary embodiment.
Figure 1B:
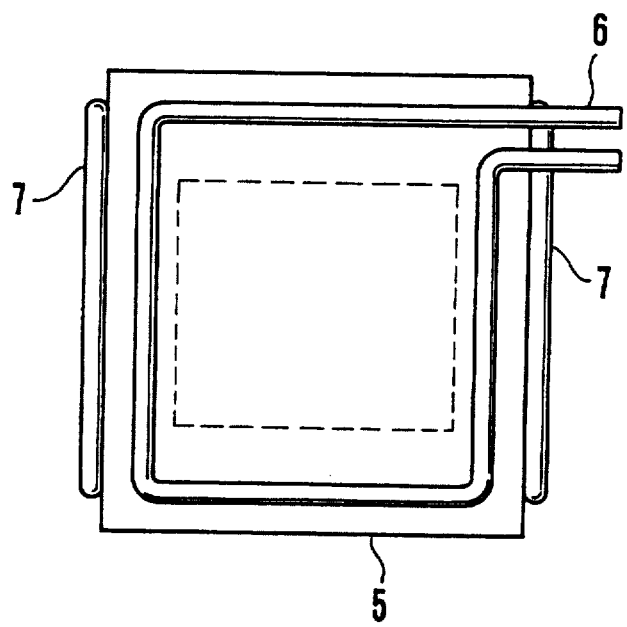
FIG. 1B is a plan of the same.

FIG. 1A shows in a sectional view a structure of the non-destructive sectional shape inspecting apparatus according to an embodiment of the invention, and FIG. 1B is a plan view of the same. An object or specimen 1 under test is disposed on a supporting base 3 and placed within a specimen chamber 5 at the center thereof. In the case of the illustrated embodiment, it is assumed that the specimen under test (i.e. object for inspection) is a product made of a synthetic resin material by a precision lost-wax process. According to this process, a wax mold is used for forming the interior of the product. Thus, the product has a hollow interior and is, so to say, of a bag-like configuration having an opening for allowing the wax to be removed by melting after the forming. Heretofore, in the inspection of this sort of product in respect to the shape of the plane section, it has practically been impossible to measure the thickness of the section.

The specimen chamber 5 of the illustrated embodiment includes a signal generating material cell 4 filled with a solution of nuclear magnetic resonance material (i.e. a solution of a material capable of emitting nuclear resonance signal). The signal generating material cell 4 is formed of an acrylic resin, and an aqueous solution of cupric sulfate is used as the signal generating material. Cupric sulfate is effective for decreasing relaxation time of atomic nuclei of hydrogens contained in water and intensifying the nuclear magnetic resonance signal. It should however be understood that ordinary water as well as pure water containing no impurities may also be used as the signal generating material 2 at the expense of more or less decrease in the available amount of signal. The signal generating solution 2 is injected through an injection pipe 8 (a nozzle of non-magnetic material) inserted into a bore of small diameter formed in the specimen 1 under test, whereby the inner space (hollow interior) is filled with the signal generating solution 2 until it overflows into the signal generating cell 4. In this way, the cell 4 is filled with the signal generating material 2. Disposed around the specimen chamber 5 are an irradiation coil 6 and a sense coil 7 for detecting the nuclear magnetic resonance signal generated within the specimen chamber 5.

When the interior of the signal generating solution cell 4 is imaged by processing appropriately the nuclear magnetic resonance signal, plane section of the specimen 1 under test makes appearance in the form of a region where no nuclear magnetic resonance signal is generated.

Figure 2:
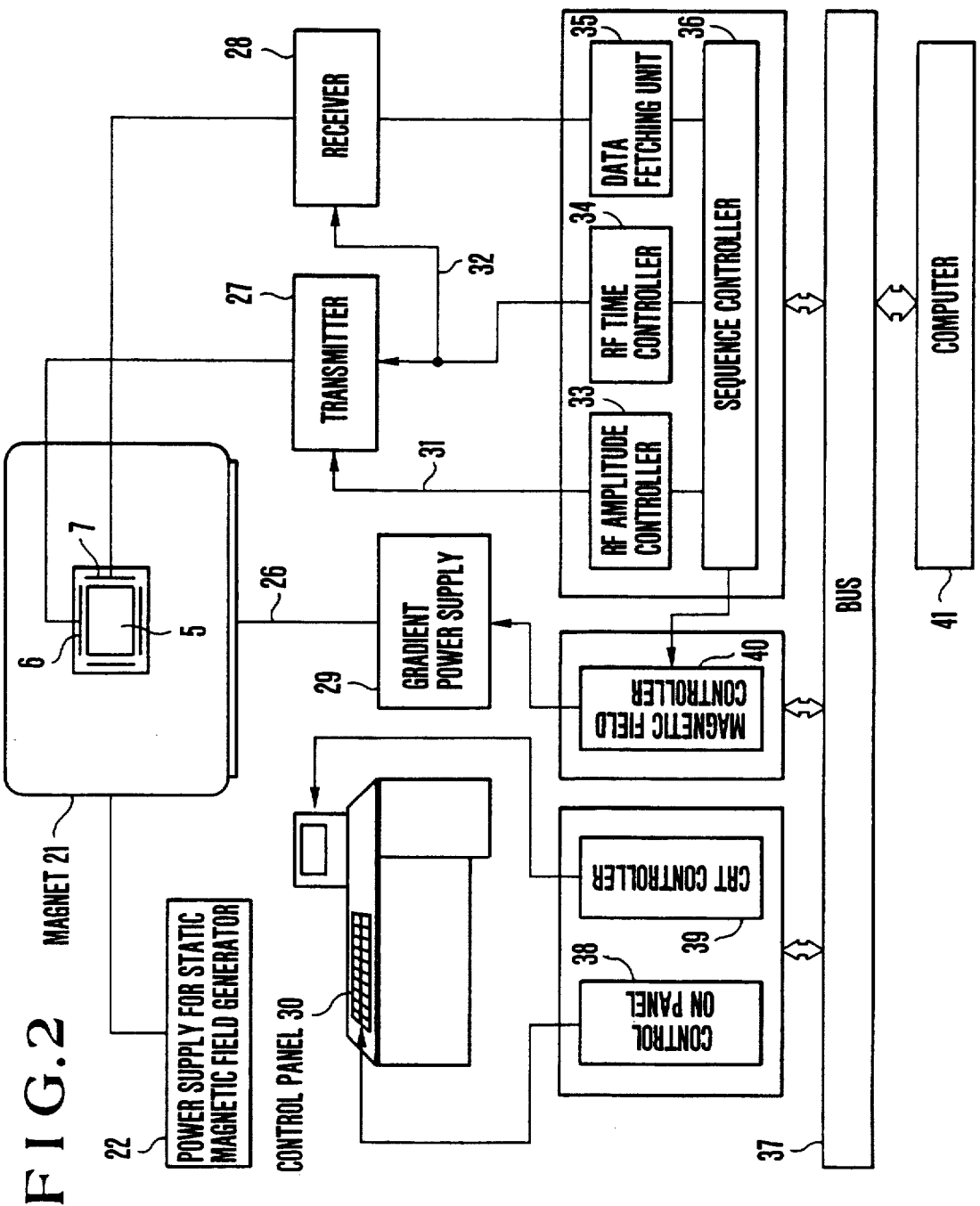
FIG. 2 is a block diagram showing a general arrangement of a non-destructive sectional shape inspecting apparatus according to an embodiment of the invention.

FIG. 2 shows a general arrangement of the non-destructive sectional shape inspecting system according to an embodiment of the invention. A magnet 21 constitutes a major part of the system and may be composed of a superconduction type electromagnet, a normal conduction type electromagnet or a permanent magnet. In the case of the illustrated embodiment, it is assumed that the normal conduction type electromagnet is employed, by way of example only.

The normal conduction type electromagnet to this end is usually implemented in an air-core configuration for realizing a high uniformity in the magnetic field as generated. The air-core electromagnet employed in the illustrated embodiment exhibits a magnetic flux density of 0.15 T (tesla), wherein the uniformity of the magnetic field is about 50 ppm/30 cm in diameter of spherical volume. Electric current for exciting the electromagnet is supplied from a power supply 22 for a static magnetic field generator. The specimen chamber 5 is disposed at the center of the air-core electromagnet.

Gradient magnetic fields are superposed on the static magnetic field for acquiring data or information about spatial positions. A high frequency signal for giving rise to the nuclear magnetic resonance (NMR) phenomenon is supplied to the irradiation coil 6 from a transmitter 27.

The NMR signal generated by the specimen under test is detected by the sense coil 7 and supplied to a receiver 28. In the NMR measurement, a time interval intervening between application of the high-frequency magnetic field and the detection of the NMR signal is also an important factor. Accordingly, the transmitter 27 and the receiver 28 are accurately synchronized in phase with each other with the aid of a receiver gate signal 32.

A power supply 29 for generating the gradient magnetic field is constituted by three channels of constant current sources for the purpose of generating the gradient magnetic fields in three axial directions X, Y and Z, respectively. Since the gradient magnetic field is applied pulsewise, a high-speed response is required. For this reason, the pulsewise generation of the gradient magnetic field is controlled by a gradient magnetic field controller 40.

Manipulation or control of the system is realized by using a control console 30 which is provided with a variety of keys and a CRT (cathode ray tube) display for displaying the picture image as generated.

Control of the whole system as well as high-speed processing for generating the image is performed by a computer 41. Transactions between the computer 41 and various control systems are realized through a bus 37. Controlled by a sequence controller 36 are a variety of pulse sequences, the most important one of which is a combination of the high frequency magnetic field pulses and the gradient magnetic field pulses.

In FIG. 2, a reference numeral 26 designates a signal supplied to the gradient magnetic field generating coil, 31 designates an amplitude data signal, 33 denotes a RF amplitude controller, 34 denotes a RF duration time controller, 35 denotes a data fetching unit, 38 denotes the control console or panel, and 39 denotes a CRT controller.

The basic concept underlying the imaging method based on the NMR phenomenon will be elucidated below by referring to FIGS. 3 and 4.

Referring to FIG. 3 showing in a sectional view a measuring unit of the illustrated non-destructive inspection system, the electromagnet assembly is composed of four static magnetic field coils 51, wherein a gradient magnetic field coil 52, the irradiation coil 6 and the sense coil 7 are disposed within the inner space defined by the four static field coils 51. The direction of the static field is indicated by an arrow 53 and ordinarily defined as the Z-axis. The gradient magnetic fields have to be applied independent of one another in the directions corresponding to the X-, Y- and Z-axes, respectively, of a three-dimensional orthogonal coordinate system. To satisfy this requirement, three coils are used for the X-, Y- and Z-directions, respectively. In FIG. 3, reference numerals 54, 55, 56 and 57 denote connections to the receiver 26, the transmitter 27, the power supply unit 29 for generating three channels of the gradient magnetic fields and the power supply for generating the static magnetic field, respectively.

FIG. 4 is a view for illustrating an example of the pulse sequences.

In FIG. 4, there are illustrated sequentially from the top a high frequency power pulse waveform 61 with which a specimen under test is irradiated through coil 6, a signal 62 resulting from amplification of the electromotive force induced in the sense coil 7, a Z-gradient magnetic field 63 applied in the Z-direction which is same as that of the static magnetic field, a Y-gradient magnetic field 64 applied in the Y-direction in the form of phase encode pulse, and an X-gradient magnetic field 65 applied in the X-direction for establishing one-to-one correspondence between the coordinate position along the X-axis and the resonance frequency. The X-gradient field 65 is usually employed for generating spin echoes and regarded as the reading gradient magnetic field. A reference numeral 66 denotes a time axis for clarifying the temporal relations among the pulse signals shown above the axis.

Next, description will be made in more detail concerning the roles of these various pulses and the principle underlying an image reconstituting method referred to as a two-dimensional Fourier method.

In the case of the example illustrated in FIG. 4, the waveform 61 of a high frequency power can be represented by a sinc function. The Fourier transformation of the sinc function results in a rectangular waveform. In other words, the sinc function in the time space represents a rectangular waveform in the frequency space and thus has only a frequency limited in the range. As can be seen in FIG. 4, a gradient field pulse 70 is applied in the Z-direction simultaneously with the 90°-pulse (high frequency pulse for tilting the nuclear spin by 90°) 67.

In the NMR phenomenon, the resonance condition is given by the following expression:

$$ti \ W_O = 2\pi f_O = \gamma[H_O + H_G(Z)] \quad (1)$$

where $f_O$ represents a resonance frequency, $W_O$ represents an angular velocity at the resonance point, $Y$ represents a magnetic rotation rate, $H_O$ represents a magnetic flux density of the static field, and $H_G(Z)$ represents the magnetic flux density of the gradient field at the position Z. Accordingly, only a specific plane section in the Z-direction that emits a resonance frequency equal to that of the rectangular waveform resulting from the Fourier transformation of the sinc function is selectively excited Ordinarily, the frequency for the selective irradiation is so established that the thickness of a plane section layer lies in a range of 1 to 20 mm. In the case of illustrated embodiment, a 180°-pulse is applied in succession to the 90°-pulse to derive a spin echo signal 69. Parenthetically, it should be mentioned that according to the original two-dimensional fourier method, the spin echo is generated by applying the gradient magnetic field instead of using the 180°-pulse.

A feature characterizing the spin echo method is seen in that phase diverging rapidly at an apparent horizontal relaxation time $T_2$ due to non-uniform magnetic field is again aligned after lapse of a predetermined time. The gradient magnetic field is also one species of the non-uniform magnetic field. Accordingly, in order to derive the signal having aligned phase, the gradient field must be inverted for thereby rotating the diverging phase in the direction in which the convergence takes place or alternatively a 180°-pulse is applied for thereby applying a same gradient magnetic field as that applied for diverging the phase for the purpose of rotating the phase in the converging direction. In reality, in application of the gradient magnetic field, the rise-up time and the fall time of the magnetic field are finite (practically on the order of 1 ms). During such transient period, phase is disturbed. To compensate for the phase disturbances, the compensating pulse 71 is applied in succession to the gradient field pulse 70 to cancel out the disturbances. In this way, the condition equivalent to the application of the true rectangular waveform field in appearance is realized.

Next, description will be turned to the phase encoding.

The phase encode pulse field is a gradient magnetic field applied by varying the intensity and the time of application by predetermined amounts, respectively, for deriving the pixel information in the longitudinal direction. The pixel information in the transverse direction can be obtained by sampling the echo signals generated every phase encode pulse at a sampling frequency corresponding to the number of pixels in the transverse direction. Data obtained by applying a series of phase encode pulses are then subjected to the two-dimensional Fourier transformation to obtain ultimately a tomographic image.

In the case of the illustrated embodiment, the phase encode pulse is the Y-gradient field 64. Since magnitude of the phase encode is determined by a value resulting from integration of the encoding gradient magnetic field pulse 74, the abovementioned magnitude can be determined by varying amplitude or width of the phase encode pulse. In the exemplary case illustrated in FIG. 4, the amplitude is varied. For establishing accurately magnitude of the phase encode, it is necessary to apply the pulse of rectangular waveform. However, in reality, the pulse has inevitably a rise-up slope (edge) and a fall slope. With a view to cancelling out the rise-up and fall transients to thereby realize the same effect as that obtained by applying the phase encode pulse having an essentially rectangular waveform, a phase encode pulse 73 having the same waveform as that of the rise-up edge and the fall edge is applied in precedence to the phase encode pulse 74. Although both the phase encode pulses 73 and 74 represent the gradient magnetic fields of a same polarity, they can serve to cancel out the rise-up and fall transients because of interposition of the 180°-pulse 68 between the pulses 73 and 74, as the result of which the same effect as that obtained by application of the phase encode pulse of rectangular waveform can be realized.

The X-gradient magnetic field 65 is applied in the X-direction. When the gradient magnetic field of the X-direction is applied to spin in the state of coherent precession excited by the 90°-pulse 67, the frequency of the precession in the X-direction varies linearly in proportion to the intensity of the X-gradient magnetic field. In succession to the 180°-pulse 68, a same gradient magnetic field is applied to converge again the phase, and the spin echo signal 69 resulting therefrom is detected. Since the X-coordinates representing the positional information bear a linear relation to the resonance frequencies, it is possible to determine the relations of the signal intensities to the X-coordinates through Fourier transformation of the spin echo signal 69. The relations thus determined are again subjected to Fourier transformation to determine the relations of signal intensities relative to the Y-coordinates. In this way, signal distribution for an X-Y plane is obtained. By displaying the signal intensities on the X-Y plane on a CRT screen, a tomographic image can be generated.

When a thickness distribution along a section, for example, of a bag-like product or specimen formed of a synthetic resin by a precision forming is to be inspected by making use of the nuclear magnetic resonance (NMR) phenomenon by enclosing the specimen with a volume of material capable of generating a NMR signal, a solution of the material is injected into the bag-like product and subsequently the signal generating substance cell 4 disposed within the specimen chamber 5 is filled with the solution of the material capable of generating the NMR signal. The bag-like specimen is then immersed within the solution in the cell 4, whereon the tomography process is performed by the NMR plotting method based on the two-dimensional or three-dimensional Fourier image reconstitution procedure. Then, a plane section of the formed product or specimen under test makes appearance in the form of a region where the NMR signal is absent. In the three-dimensional image reconstituting method, the tomographic images of the specimen under test as taken in the various directions can be obtained through appropriate image processing performed on the data derived as three-dimensional information.

In the case of the two-dimensional Fourier image reconstituting method, the tomographic images of a sample under test as observed in various directions can be obtained by applying a gradient magnetic field resulting from vector synthesization of the magnetic fields of X-, Y- and Z-directions and measuring the resonance signals.

In conjunction with the specimen to be inspected, it should be added that sections of the specimen under test can be visually generated independent of the material forming the specimen except for a metallic material interfering the nuclear magnetic resonance. Besides, since the NMR phenomenon can be observed by using only the magnetic field (90°-pulse) and the electromagnetic wave (180°-pulse), the specimen or sample under test can not suffer from any injury. In the case of the illustrated embodiment, the material capable of generating the NMR signal is used in the form of a liquid solution. However, the invention is not restricted to the use of such solution but can equally be carried out by using a gas containing elements having hydrogen atoms such as, for example, a hydrogen gas.

As other examples of the materials capable of generating the NMR signal, there may be mentioned materials of silicon series, fluidized pulverized solid material containing hydrogen atoms, silicone-series rubber susceptible to change from liquid to solid phase under predetermined conditions.

I claim:

1. A non-destructive sectional shape inspecting apparatus, comprising:
   (a) means for at least surrounding an exterior of an object under test with a material capable of reradiating a nuclear magnetic resonance signal;
   (b) means for applying a radio frequency pulse to said object under test;
   (c) means for applying a gradient magnetic field to said object;
   (d) means for detecting said nuclear magnetic resonance signal;
   (e) means for performing Fourier transformation upon said detected signal to obtain an image signal;
   (f) means for extracting data corresponding to a sectional image signal of said object from said Fourier transformed image signal; and
   (g) image processing means for obtaining a sectional image of said object from said extracted data.

2. A non-destructive sectional shape inspecting apparatus according to claim 1, wherein said material capable of reradiating the nuclear magnetic resonance signal is a liquid.

3. A non-destructive sectional shape inspecting apparatus according to claim 2, wherein said liquid is an aqueous solution of cupric sulfate.

4. A non-destructive sectional shape inspecting apparatus according to claim 2, wherein said liquid is water.

5. A non-destructive sectional shape inspecting apparatus according to claim 4, wherein said liquid is pure water.

6. A non-destructive sectional shape inspecting apparatus according to claim 1, wherein said material capable of reradiating the nuclear magnetic resonance is a gas.

7. A non-destructive sectional shape inspecting apparatus according to claim 6, wherein said gas is a gas containing hydrogen atoms.

8. A non-destructive sectional shape inspecting apparatus according to claim 7, wherein said gas is a hydrogen gas.

9. A non-destructive sectional shape inspecting apparatus according to claim 1, wherein said material capable of reradiating nuclear magnetic resonance signal is a solid.

10. A non-destructive sectional shape inspecting apparatus according to claim 9, wherein said solid contains elements containing hydrogen atoms.

11. A non-destructive sectional shape inspecting apparatus according to claim 9, wherein said solid is fluidized.

12. A non-destructive sectional shape inspecting apparatus according to claim 10, wherein said solid is fluidized.

13. A non-destructive sectional shape inspecting apparatus according to claim 11, wherein said fluidized solid is composed of particles of a small size.

14. A non-destructive sectional shape inspecting apparatus according to claim 12, wherein said fluidized solid is composed of particles of a small size.

15. A non-destructive sectional shape inspecting apparatus according to claim 9, wherein said solid is a material of silicon series.

16. A non-destructive sectional shape inspecting apparatus according to claim 1, wherein said material capable of reradiating the nuclear magnetic resonance signal is a rubber of silicone series.

17. A non-destructive sectional shape inspecting apparatus according to claim 1, wherein said means for applying the gradient magnetic field includes:
   (1) means for vector-synthesising the gradient magnetic fields to determine predetermined field intensity and direction; and
   (2) means for applying said vector-synthesised gradient magnetic field.

18. A non-destructive sectional shape inspecting apparatus comprising:
   (a) means for filling internally and externally surrounding a hollow object under test with a material capable of reradiating a nuclear magnetic resonance signal which differs from that reradiated from said object under test;
   (b) means for applying a radio frequency pulse to said object under test;
   (c) means for applying a gradient magnetic field to said object;
   (d) means for detecting said nuclear magnetic resonance signal;
   (e) means for performing Fourier transformation upon said detected signal to obtain an image signal;

(f) means for extracting data corresponding to the nuclear magnetic resonance signal reradiated by said object from said Fourier transformed image signal; and (g) image processing means for obtaining a sectional image of said object from said extracted data.

19. A non-destructive sectional shape inspecting method, comprising:

(a) a step of at least externally surrounding an object under test with a material capable of reradiating a nuclear magnetic resonance signal which differs from that reradiated by said object;

(b) a step of applying a radio frequency pulse and a gradient magnetic field to said object under test;

(c) a step of detecting said nuclear magnetic resonance signal;

(d) a step of performing Fourier transformation upon said detected signal to obtain an image signal;

(e) a step of extracting data corresponding to a sectional image signal of said object from said Fourier transformed image signal; and (f) a step of obtaining a sectional image of said object from said extracted data.

20. An inspecting method according to claim 19, wherein said step of applying the gradient magnetic field includes:

(1) a step of vector-synthesising the gradient magnetic fields to determine predetermined field intensity and direction; and (2) a step of applying said vector-synthesised gradient magnetic field.

21. A non-destructive sectional shape inspecting method, comprising:

(a) a step of filling internally and externally surrounding a hollow object under test with a material capable of reradiating a nuclear magnetic resonance signal;

(b) a step of applying a radio frequency pulse and a gradient magnetic field to said object under test;

(c) a step of detecting said nuclear magnetic resonance signal;

(d) a step of performing Fourier transformation upon said detected signal to obtain an image signal;

(e) a step of extracting data corresponding to a sectional image signal of said object from said Fourier transformed image signal; and (f) a step of obtaining a sectional image of said object from said extracted data.

22. An inspecting method according to claim 21, wherein said step of applying the gradient magnetic field includes:

(1) a step of vector-synthesising the gradient magnetic fields to determine predetermined field intensity and direction; and (2) a step of applying said vector-synthesised gradient magnetic field.

23. A non-destructive sectional shape inspecting apparatus according to claim 1, wherein said object under test has a hollow interior and said means for at least surrounding the exterior of said object includes means for filling the interior of said object with said material capable of reradiating a nuclear magnetic resonance signal so that both the interior and exterior of said object contacting said material.

24. A non-destructive sectional shape inspecting apparatus according to claim 23, wherein said means for extracting data utilizes one of a two-dimensional and three-dimensional image reconstruction so that a wall separating the interior from the exterior of said object is represented by said extracted data obtained from an area in which said nuclear magnetic resonance signal is one of absent and weaker than that of an environmental area.

25. A non-destructive sectional shape inspecting apparatus according to claim 18, wherein said means for extracting data utilizes one of a two-dimensional and three-dimensional image reconstruction.

26. A non-destructive sectional shape inspecting method according to claim 19, wherein said object under test has a hollow interior and said step of surrounding the exterior of said object includes filling the interior of said object with said material capable of reradiating a nuclear magnetic resonance signal so that both the interior and exterior of said object contacts said material.

27. A non-destructive sectional shape inspecting method according to claim 25, wherein said step of extracting data includes utilizing one of two-dimensional and three-dimensional image reconstruction.

28. A non-destructive sectional shape inspecting method according to claim 21, wherein said step of extracting data includes utilizing one of a two-dimensional and three-dimensional image reconstruction so that a wall separating the interior from the exterior of said object is represented by said extracted data obtained from an area in which said nuclear magnetic response signal is one of absent and weaker than an environmental area.

* * * * *